US012758350B2

(12) United States Patent
Wang et al.

(10) Patent No.: US 12,758,350 B2
(45) Date of Patent: Oct. 13, 2026

(54) MICROSURGERY AUXILIARY DEVICE

(71) Applicant: ZUMAX MEDICAL CO., LTD, Suzhou City (CN)

(72) Inventors: Jilong Wang, Suzhou City (CN); Jin He, Suzhou City (CN); Jianyue Li, Suzhou City (CN); Lei Du, Suzhou City (CN); Chengjie Zhu, Suzhou City (CN)

(73) Assignee: ZUMAX MEDICAL CO., LTD., Suzhou City (CN)

( * ) Notice: Subject to any disclaimer, the term of this patent is extended or adjusted under 35 U.S.C. 154(b) by 501 days.

(21) Appl. No.: 18/027,646

(22) PCT Filed: Apr. 25, 2021

(86) PCT No.: PCT/CN2021/089570
§ 371 (c)(1),
(2) Date: Mar. 22, 2023

(87) PCT Pub. No.: WO2022/062383
PCT Pub. Date: Mar. 31, 2022

(65) Prior Publication Data

US 2023/0372048 A1 Nov. 23, 2023

(30) Foreign Application Priority Data

Sep. 23, 2020 (CN) ......................... 202011009438.8

(51) Int. Cl.
*A61B 90/25* (2016.01)
*A61B 90/00* (2016.01)
*A61B 90/30* (2016.01)

(52) U.S. Cl.
CPC .............. *A61B 90/25* (2016.02); *A61B 90/30* (2016.02); *A61B 2090/309* (2016.02); *A61B 2090/372* (2016.02)

(58) Field of Classification Search
CPC ......... A61B 90/20; A61B 90/25; A61B 90/30; A61B 90/37; A61B 2090/309;
(Continued)

(56) References Cited

U.S. PATENT DOCUMENTS 5,140,458 A * 8/1992 Takagi ................. G02B 21/082 359/380
5,266,791 A * 11/1993 Morizumi .............. G02B 21/22 250/201.3
(Continued)

FOREIGN PATENT DOCUMENTS

CN 101842731 A 9/2010
CN 103364934 A 10/2013
(Continued)

OTHER PUBLICATIONS

Wikipedia, "Optical spectrometer", https://en.wikipedia.org/wiki/Optical_spectrometer, accessed online on Jul. 23, 2025 (Year: 2025).*

(Continued)

*Primary Examiner* — Stephone B Allen
*Assistant Examiner* — Adam W Booher
(74) *Attorney, Agent, or Firm* — Zhong Law, LLC

(57) ABSTRACT

A microsurgery auxiliary device provided in the present invention, comprises a lens body (1) and a naked eye 3D display (2), the lens body (1) being internally provided with an imaging unit (10); the imaging unit (10) comprises a large objective lens group (11), a zoom lens group (12), a first tube objective lens (13) and a photosensitive element (14); the large objective lens group (11), the zoom lens group (12), the first tube objective lens (13) and the photosensitive element (14) are sequentially located in the same observation optical path; the large objective lens group (11) comprises at least one positive lens group (111) and at least one negative lens
(Continued)

group (112), the positive lens group (111) and the negative lens group (112) are arranged in the same optical axis, and the spacing between the positive lens group (111) and the negative lens group (112) is adjustable; and the naked eye 3D display (2) is connected to the photosensitive element (14), the distance between the naked eye 3D display (2) and an observer (5) is 400-1200 mm, and the viewing angle range of the naked eye 3D display (2) is not less than 120 degrees. The observer can directly perform surgical operations by observing the naked eye 3D display (2), the overall structure of the device is simple, and the system delay is small.

10 Claims, 5 Drawing Sheets

(58) Field of Classification Search
CPC ........ A61B 2090/371; A61B 2090/372; G02B 21/0012; G02B 21/02; G02B 21/025; G02B 21/06; G02B 21/08; G02B 21/082; G02B 21/18; G02B 21/20; G02B 21/22; G02B 21/36; G02B 21/361; G02B 21/362; G02B 21/368; G02B 7/001
See application file for complete search history.

(56) References Cited

U.S. PATENT DOCUMENTS

| | | | | |
|---|---|---|---|---|
| 5,657,128 | A | 8/1997 | Miller et al. | |
| 2003/0151809 | A1* | 8/2003 | Takahashi | H04N 13/32 348/E13.031 |
| 2014/0340501 | A1 | 11/2014 | Hauger et al. | |
| 2015/0160448 | A1 | 6/2015 | Hong et al. | |
| 2017/0293129 | A1 | 10/2017 | Hatakeyama et al. | |
| 2017/0293132 | A1* | 10/2017 | Omote | G02B 5/04 |
| 2018/0307022 | A1* | 10/2018 | Wicker | G02B 27/58 |
| 2019/0037210 | A1* | 1/2019 | Zhang | H04N 13/302 |
| 2020/0110956 | A1* | 4/2020 | Fan | H04N 21/42204 |

FOREIGN PATENT DOCUMENTS

| | | | |
|---|---|---|---|
| CN | 105319696 | A | 2/2016 |
| CN | 106842532 | A | 6/2017 |
| CN | 108135740 | A | 6/2018 |
| CN | 110892305 | A | 3/2020 |
| CN | 112220568 | A | 1/2021 |
| DE | 102013019096 | A1 | 5/2015 |
| JP | 2004004549 | A | 1/2004 |
| JP | 2018194698 | A | 12/2018 |

OTHER PUBLICATIONS

Graham, The Xybix Blog, "Monitor Distance and Viewing Angles: Is Your imaging Desk Set Up Properly?", https://blog.xybix.com/how-many-monitors-can-you-place-on-an-imaging-desk, available online at least as of May 8, 2015, Accessed on Jan. 12, 2026 (Year: 2015).*

Lenovo, Glossary, "What is a viewing angle?", https://www.lenovo.com/us/en/glossary/viewing-angle/, available online at least as of and accessed on Jan. 12, 2026 (Year: 2026).*

International Search Report mailed on Mar. 31, 2022 for International Application No. PCT/CN2021/089570 filed on Apr. 25, 2021, 8 Pages.

European Search Report recieved for European Patent Application No. 21870772.7, maied on Feb. 13, 2024, pp. 12.

Hoegele Artur: "Afocal zoom lenses for stereo surgical microscopes", SPIE Proceedings; [Proceedings of SPIE ISSN 0277-786X], SPIE, US, vol. 11106, available at "https://www.spiedigitallibrary.org/conference-proceedings-of-spie/11106/1110607/Afocal-zoom-lenses-for-stereo-surgical-microscopes/10.1117/12.2528170.short", published on Sep. 9, 2019, pp. 11.

Watson Jeffrey R et al: "Augmented microscopy: real-time overlay of bright-field and near-infrared fluorescence images", Journal of Biomedical Optics, SPIE, 1000 20th St. Bellingham WA 98225-6705 USA, vol. 20, No. 10, available at "https://www.spiedigitallibrary" published in Oct. 2015, pp. 10.

* cited by examiner (a)

(b)

MICROSURGERY AUXILIARY DEVICE

RELATED APPLICATION

This application is a National Stage Application of International Application No. PCT/CN2021/089570 filed on Apr. 25, 2021 which further claims priority from CN Patent Applications having Ser. No. 20/201,1009438.8 respectively filed on Sep. 23, 2020, which is incorporated herein by reference for all purpose.

FIELD OF THE INVENTION

The present invention relates to the technical field of medical equipment, in particular to a microsurgery auxiliary device.

BACKGROUND TECHNOLOGY

Microsurgery is a delicate surgery with the help of magnifying equipment. When a surgery is performed under a traditional optical surgery microscope, tissues are magnified, small tissues that are unclear to naked eyes can be seen clearly during the surgery, and have a three-dimensional sense. Therefore, surgeons can dissect, cut and suture various tissues accurately. However, even surgeons quite experienced in suturing blood vessels with naked eyes, without special training, are still not used to microsurgery at the very beginning, and often have uncoordinated hands and eyes, surgical operations under a microscope are thus affected. Therefore, a period of training and adaptation is required to skillfully perform the operations under the surgery microscope.

As the position of an exit pupil of an eyepiece of a surgery microscope is fixed and the diameter of the exit pupil is generally only about 2 mm, in order to observe a complete object plane field of view, an operator is required to keep the pupil of the eye at the position of the exit pupil of the eyepiece for a long time. Therefore, even if the design of the microscope conforms to ergonomics, the operator gets tired easily due to keeping a constant posture for a long time. For certain special affected parts, a surgery microscope needs to be greatly tilted for observation. At this time, the operator still needs to follow the eyepiece to adjust his/her position. Although some surgery microscopes are equipped with compensation structures, the compensation range is mostly limited, and operation and adjustment are required.

Based on the above reasons, in some technical solutions, a display is adopted to display video images, but an ordinary display cannot reflect depth information and is not suitable for real-time operations.

In some other technical solutions, a 3D display based on a principle of polarization is adopted, and an observer needs to wear polarized glasses to see a three-dimensional image, which is not friendly to an operator who wears glasses. Moreover, as a pixel-level microstructure of an FPR optical film is difficult to be further reduced, the size of the display in such solutions is usually large, the distance between the display and the operator is usually more than 2 meters, and the observer needs to almost directly face the display to observe an ideal three-dimensional image. When observing objects with a large distance difference, the crystalline lens needs an adjustment process, so when the operator looks away from a display at a long distance to observe and adjust parameters of a microscope or other auxiliary equipment at a short distance, the eye needs to focus again, which adversely affects observation continuity. The loss of optical energy caused by polarization may also reduce subjective brightness of human eyes and easily cause visual fatigue.

CN109147913A discloses a dual-path synchronous miniature image display system and method for a surgery microscope. The system comprises a surgery microscope, a processing device, a naked eye 3D display and a projection screen. The processing device comprises two output ends and a processing module. The processing module receives a surgery image, performs space transformation according to three-dimensional vertex coordinates of a primitive to obtain a rendered image, obtains a single depth image according to the rendered image, synthesizes a multi-viewpoint image according to the single depth image, and synchronously outputs the multi-viewpoint image to the naked eye 3D display and the projection screen through two output ends. According to this technical solution, learning and exchange effects of a surgery based on a surgery microscope can be improved, but acquired images need to be subjected to data conversion and processing, so that image delay is greatly increased, and the solution can only be used for learning and exchange but is not suitable for actual microsurgery.

CN111045202A discloses a surgery microscope, which comprises an illumination system, an imaging system and an image processing system. Multiple paths of optical imaging subsystems are adopted for simultaneous imaging, different optical imaging systems correspond to different imaging functions, a left eye view and a right eye view with large depths of field and high resolutions are obtained through fusion calculation of images with multiple optical paths and multiple functions, and then the two images are subjected to 3D interlacing. A finally-obtained 3D image of an object has obviously reduced depth sense, effectively improved definition, and the characteristics of large depths of field and high resolutions. At the same time, the microscope has good use comfort, which can well meet application needs of doctors. This solution also requires complex data processing on acquired images, which is difficult to meet low delay requirements of microsurgery. In addition, an eight-optical path imaging system with a complex structure and high manufacturing cost is required.

Therefore, in combination with above technical problems, a new technical solution is essential.

SUMMARY OF THE INVENTION

The present invention aims to provide a microsurgery auxiliary device. An observer can directly perform surgical operations by observing a naked eye 3D display. The whole structure of the device is simple, the system delay is small, a fixing mode of the naked eye 3D display can be selected according to field requirements, the fixing structure is simple and reliable, an observation component can be additionally arranged when necessary, and traditional visual observation is realized.

To achieve the aim, according to one aspect, the present invention provides a microsurgery auxiliary device, comprising a lens body and a naked eye 3D display. The lens body is internally provided with an imaging unit; the imaging unit comprises a large objective lens group, a zoom lens group, a first tube objective lens and a photosensitive element; the large objective lens group, the zoom lens group, the first tube objective lens and the photosensitive element are sequentially located in the same observation optical path; the large objective lens group comprises at least one positive lens group and at least one negative lens group, the positive lens group and the negative lens group are arranged in the same optical axis, and the distance between the positive lens group and the negative lens group is adjustable, the naked eye 3D display is connected to the photosensitive element, the distance between the naked eye 3D display and an observer is 400-1200 mm, and the viewing angle range of the naked eye 3D display is not less than 120 degrees.

In a further embodiment, the positive lens group comprises at least two optical lenses made of different materials, and the negative lens group comprises at least two optical lenses made of different materials. The negative lens group is close to an object to be observed, and comprises an outer side surface and an inner side surface. Both the outer side surface and the inner side surface are concave surfaces. The absolute value of the radius of curvature of the outer side surface is smaller than the absolute value of the radius of curvature of the inner side surface.

In a further embodiment, the adjustment range of the distance between the positive lens group and the negative lens group is not less than 6 mm.

In a further embodiment, the lens body is further internally provided with at least one illumination unit, the illumination light of each illumination unit can illuminate an object to be observed through the large objective lens group, and the direction of the illumination light entering the large objective lens group is parallel to the direction of the optical axis of the large objective lens group. The illumination unit comprises a light source assembly, a condensing lens group, a diaphragm and a projection lens group which are sequentially positioned in the same illumination optical path. The light source assembly comprises at least one LED light source, and at least one LED light source in the light source assembly can be driven to be switched to the illumination optical path to illuminate the object to be observed.

In a further embodiment, the projection lens group comprises at least one first lens, and the first lens can be driven to move along the optical axis direction thereof. The zoom lens group is of a continuous zoom structure and comprises at least two groups of second lenses, and the second lenses can be driven to move along respective optical axis directions.

In a further embodiment, a transmission device is further included. The projection lens group and the zoom lens group are linked through the transmission device.

In a further embodiment, the device comprises a binocular observation optical path. The microsurgery auxiliary device further comprises an observation unit. The observation unit comprises an eyepiece, a turning lens group and a second tube objective lens. The imaging unit further comprises a spectroscope group. In the same observation optical path, light sequentially passes through the large objective lens group and the zoom lens group to reach the spectroscope group. The spectroscope group splits the light into two parts, one part sequentially passes through the first tube objective lens to reach the photosensitive element, and the other part sequentially passes through the second tube objective lens, the turning lens group and the eyepiece.

In a further embodiment, the device further comprises a support. The support comprises a base, a supporting rod vertically mounted on the base, a large cross arm rotatably mounted on the supporting rod, a small cross arm rotatably mounted on the large cross arm, and a balance arm rotatably mounted on the small cross arm. The lens body and the observation unit are mounted on the balance arm. The naked eye 3D display is mounted on the large cross arm or the supporting rod. Or the microsurgery auxiliary device further comprises a base body and a connecting rod arranged on the base body. The naked eye 3D display is mounted at one end of the connecting rod, and can be placed on the ground or hung on a roof through the base body and the connecting rod.

In a further embodiment, the other end of the connecting rod is movably mounted on the base body, and the connecting rod can be driven to move along the axial direction thereof and/or can be driven to rotate by taking the axis thereof as a rotating shaft.

In a further embodiment, the size of the naked eye 3D display is between 12-16 inches. The microsurgery auxiliary device further comprises an acquisition device, a processing device and a driving device. The acquisition device can be configured to acquire position information of human eyes of an observer, and the processing device can be configured to control the driving device to act according to the acquired position information of the human eyes so as to adjust the display angle of the naked eye 3D display.

Compared with the prior art, the microsurgery auxiliary device provided by the present invention has one or more beneficial effects as follows:

(1) The microsurgery auxiliary device of the present application enables an observer to directly perform a surgical operation by observing a naked eye 3D display, the overall structure of the system is simple, complex data processing on images is not needed, and the system delay is small.

(2) According to the microsurgery auxiliary device of the present application, the naked eye 3D display is arranged within the range of 400-1200 mm, which is close to the observation distance of common clinical equipment. When the observer switches the line of sight between observing display and other equipment, human eyes do not need to repeatedly focus, time and labor are saved, brightness has no loss, and visual fatigue is reduced. Besides, a closer observation distance is in line with a human eye's habit of approaching when distinguishing details. The naked eye 3D display can be fixed with different modes according to different field conditions and using habits, and the fixing structure is simple and reliable.

(3) The microsurgery auxiliary device of the present application can be used to conveniently observe tissue structures at different depths with different magnifications.

(4) According to the microsurgery auxiliary device of the present application, the large objective lens with a variable focal length can easily change the position of a focal plane, i.e., the working distance of operation, to cover a required depth of surgery, and at the same time, a dual-optical path zoom lens group can realize observation of different magnifications, and can observe affected parts integrally and locally.

(5) According to the microsurgery auxiliary device of the present application, the observation angle does not need to be aligned, and the orientation of the display does not need to be adjusted within a common observation angle range.

(6) According to the microsurgery auxiliary device of the present application, a visual observation component may be additionally arranged when necessary, and traditional visual observation is realized.

(7) According to the microsurgery auxiliary device of the present application, the optical axis of the illumination optical path thereof is arranged in parallel to the optical axis of the large objective lens, reflection loss thus can be reduced, symmetrically dual optical paths may be arranged to enhance the illumination intensity, reduce the transverse volume of the system is compressed, and facilitate lens balance.

(8) According to the microsurgery auxiliary device of the present application, the projection lens group and the zoom lens group thereof can be linked, the size of an illumination optical spot can be simultaneously adjusted when a magnification is changed for observation, the optical damage risks possibly caused to tissues outside a field of view are reduced, the illumination inside the field of view is also favorably improved, and the reduction of subjective brightness of human eyes during high-magnification observation is compensated.

(9) According to the microsurgery auxiliary device of the present application, the naked eye 3D display thereof can also automatically track observer's eyes to ensure a best observation angle.

Figure 1:
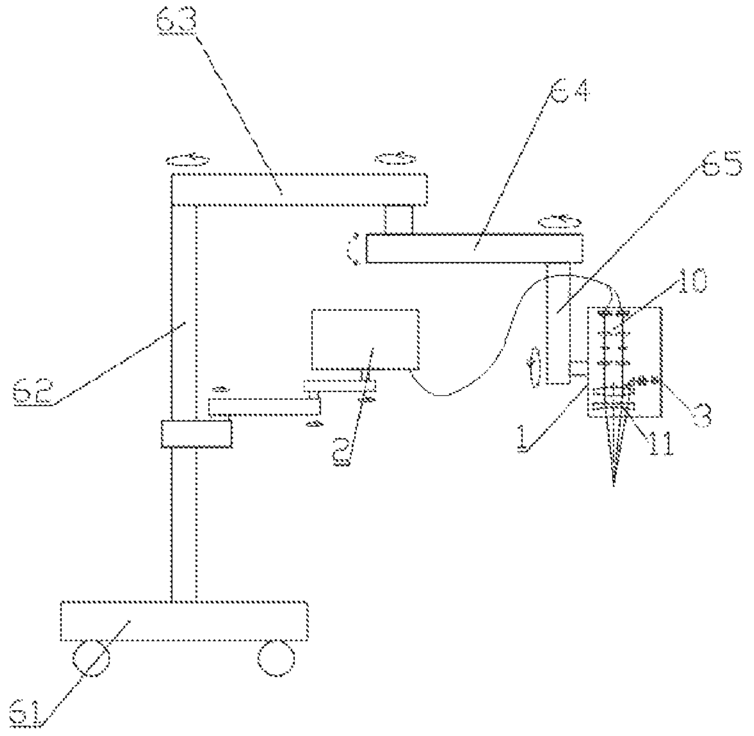
FIG. 1 is a schematic structural diagram of a microsurgery auxiliary device provided by one embodiment of the present application.
Figure 2:
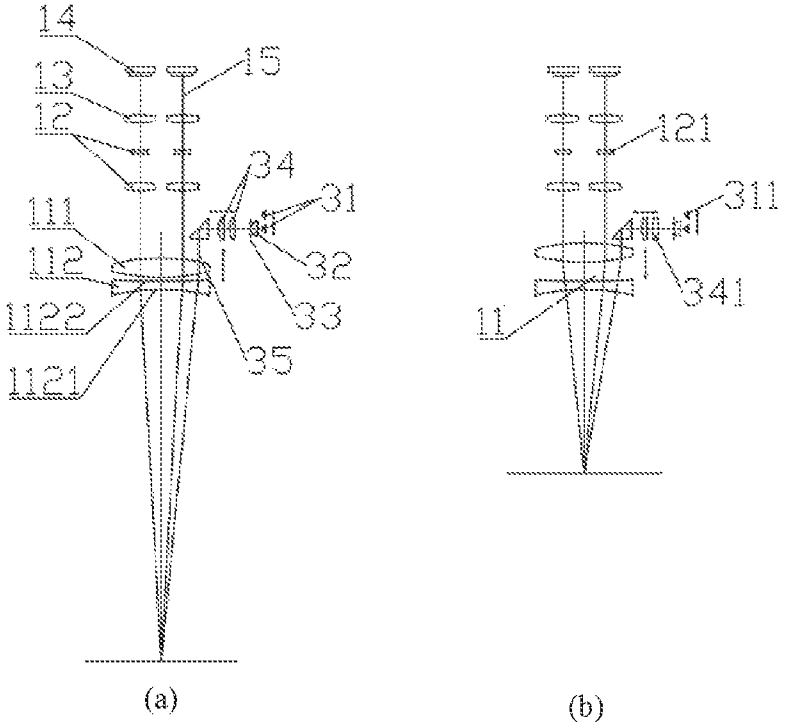
FIG. 2*a* and FIG. 2*b* are principle schematic diagrams of optical paths of a microsurgery auxiliary device provided by one embodiment of the present application in two states when the distance between a positive lens group and a negative lens group is adjusted.

In the drawings: 1—lens body, 10—imaging unit, 11—large objective lens group, 111—positive lens group, 112—negative lens group, 1121—outer side surface, 1122—inner side surface, 12—zoom lens group, 121—second lens, 13—first tube objective lens, 14—photosensitive element, 15—observation optical path, 16—spectroscope group, 2—naked eye 3D display, 21—base body, 22—connecting rod, 3—illumination unit, 31—light source assembly, 311—LED light source, 32—condensing lens group, 33—diaphragm, 34—projection lens group, 341—first lens, 35—illumination optical path, 4—observation unit, 41—eyepiece, 42—turning lens group, 43—second tube objective lens, 5—observer, 6—support, 61—base, 62—supporting rod, 63—large cross arm, 64—small cross arm, 65—balance arm.

DETAILED DESCRIPTION OF THE PREFERRED EMBODIMENTS

In order to further illustrate the technical means and effects adopted by the present invention to achieve intended aims, the specific embodiments, structures, features and effects are described in detail below in combination with the drawings and preferred embodiments.

Figure 3:
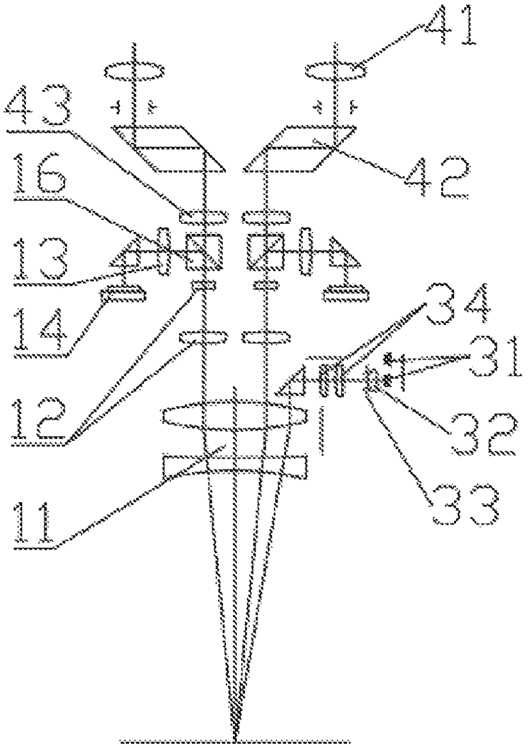
FIG. 3 is a principle schematic diagram of optical paths of a microsurgery auxiliary device provided by one embodiment of the present application with an observation unit.
Figure 4:
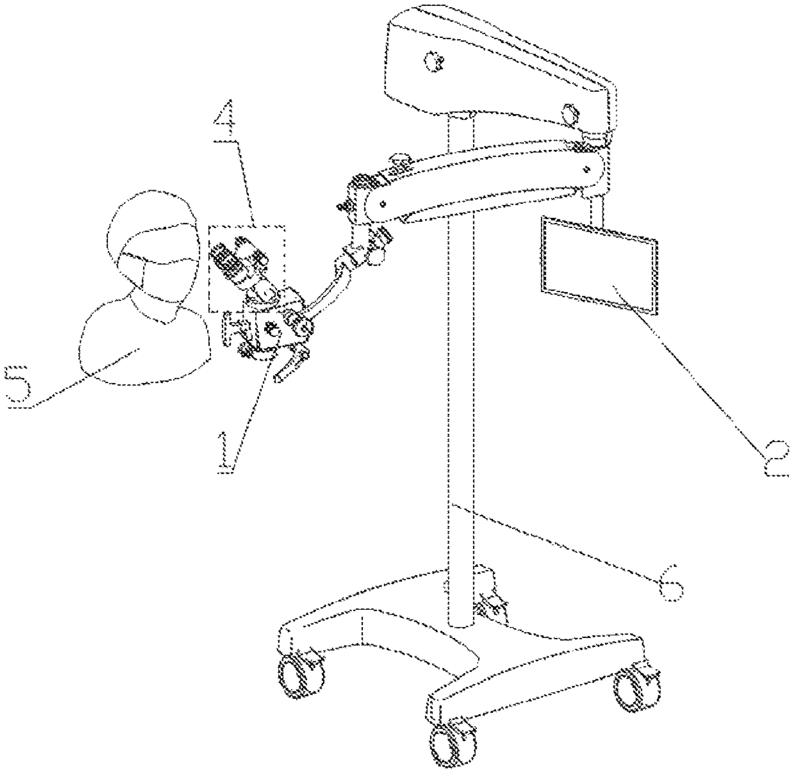
FIG. 4 is a principle schematic diagram of optical paths of a microsurgery auxiliary device provided by one embodiment of the present application without an observation unit.
Figure 5:
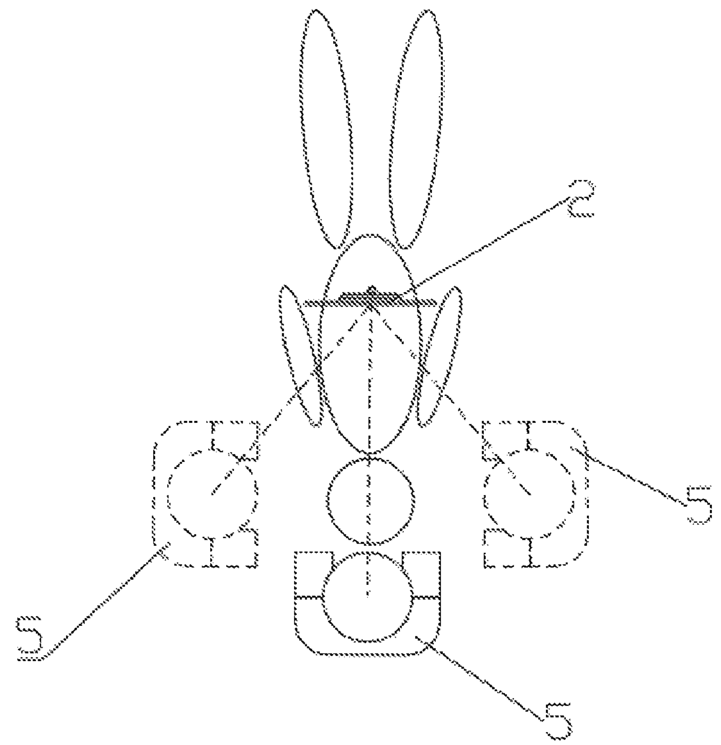
FIG. 5 is a schematic diagram of an application state of a microsurgery auxiliary device provided by one embodiment of the present application in a dental clinic.
Figure 6:
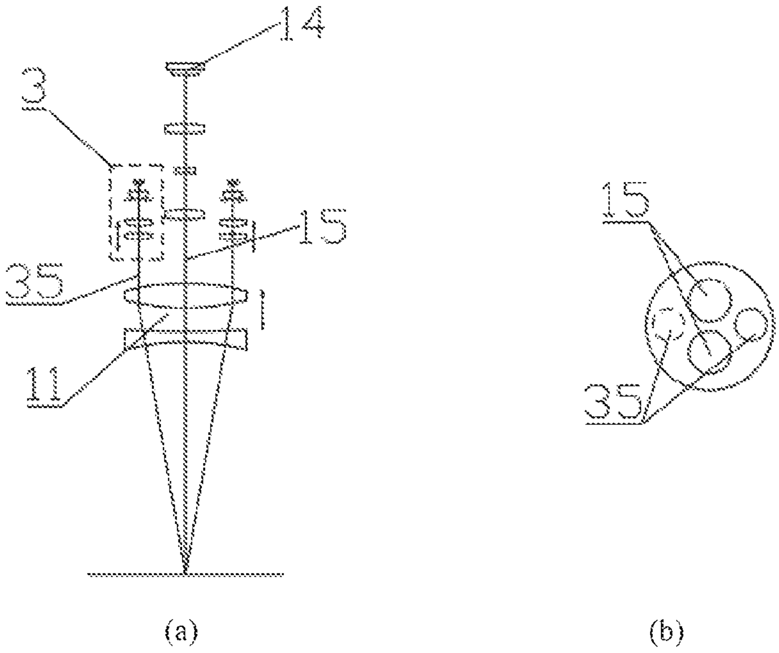
FIG. 6*a* and FIG. 6*b* are principle schematic diagrams of optical paths of a microsurgery auxiliary device provided by one embodiment of the present application with dual illumination optical paths.
Figure 7:
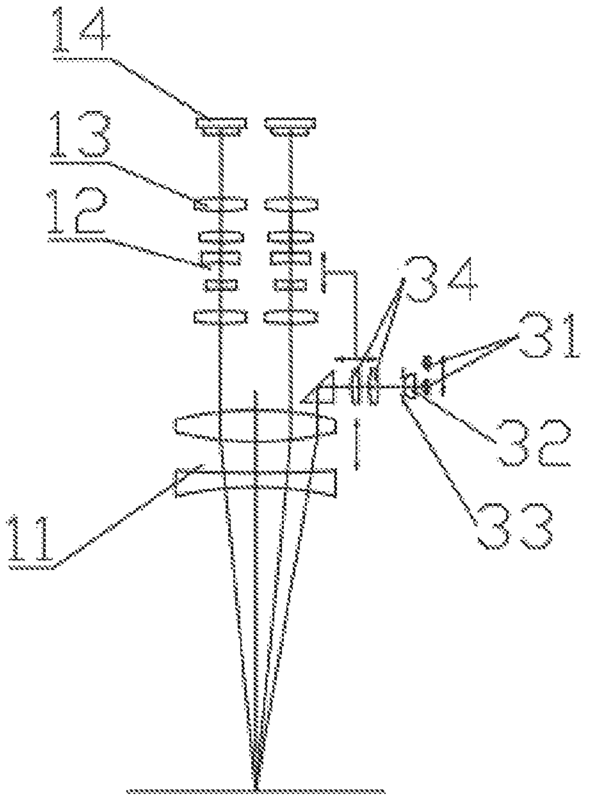
FIG. 7 is a principle schematic diagrams of optical paths of a microsurgery auxiliary device provided by one embodiment of the present application when a projection lens group and a zoom lens group are linked.
Figure 8:
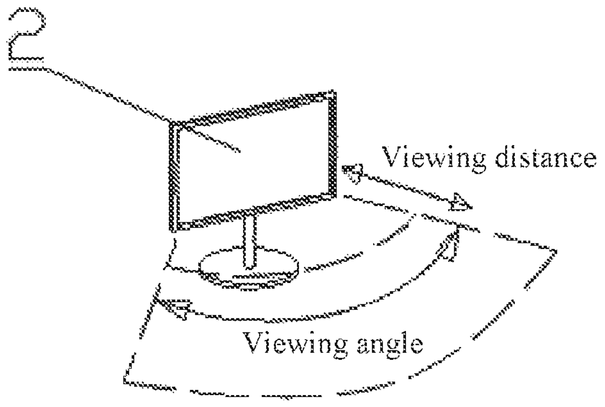
FIG. 8 is a schematic diagram of the viewing angle and the distance of a naked eye 3D display of a microsurgery auxiliary device provided by one embodiment of the present application.
Figure 9:
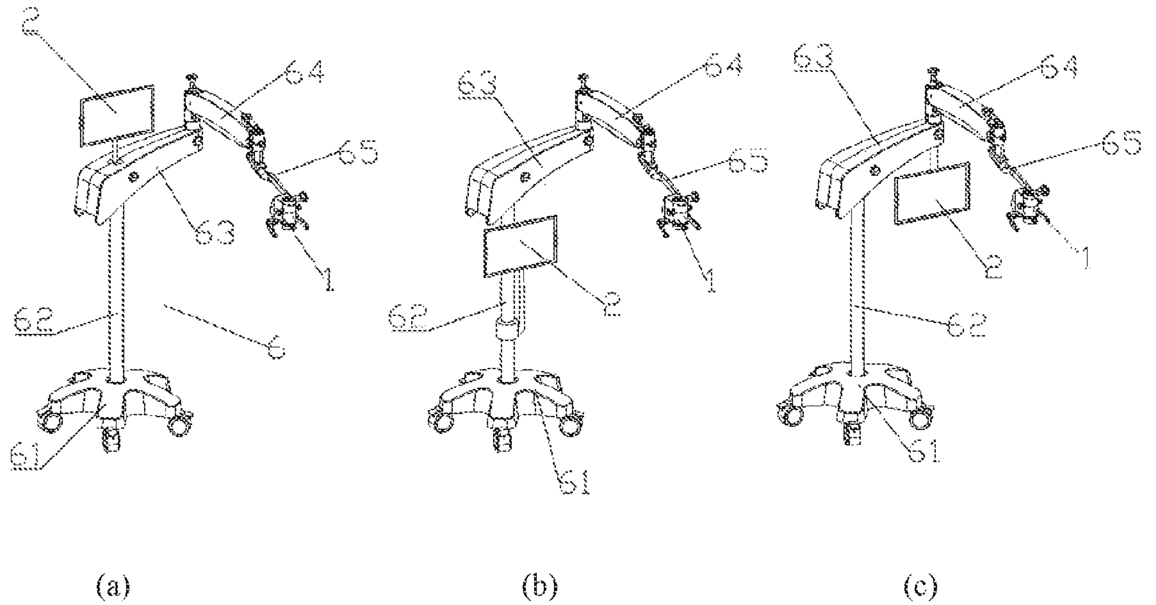
FIGS. 9*a*-9*c* are schematic structural diagrams of a microsurgery auxiliary device provided by one embodiment of the present application when a naked eye 3D display is mounted on a support.
Figure 10:
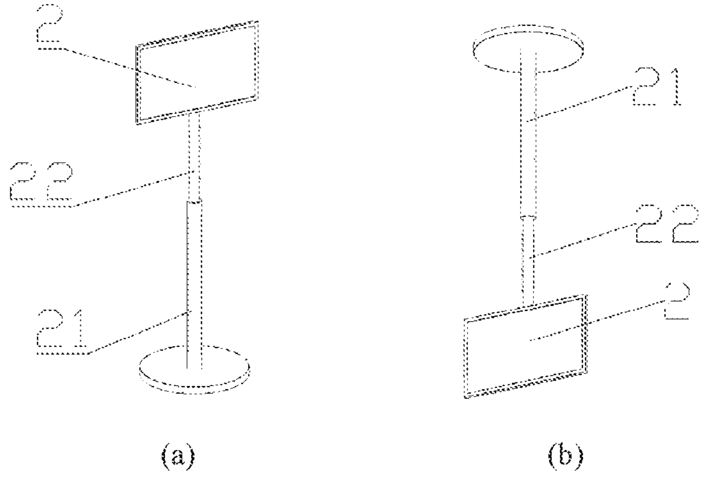
FIG. 10*a* and FIG. 10*b* are mounting schematic diagrams of a microsurgery auxiliary device provided by one embodiment of the present application when a naked eye 3D display is mounted outside a support.

Refer to FIGS. 1-10, FIG. 1 is a schematic structural diagram of a microsurgery auxiliary device provided by one embodiment of the present invention; FIG. 2*a* and FIG. 2*b* are principle schematic diagrams of optical paths of a microsurgery auxiliary device provided by one embodiment of the present invention in two states when the distance between a positive lens group and a negative lens group is adjusted; FIG. 3 is a principle schematic diagram of optical paths of a microsurgery auxiliary device provided by one embodiment of the present invention with an observation unit; FIG. 4 is a schematic structural diagram of a microsurgery auxiliary device provided by one embodiment of the present invention without an observation unit; FIG. 5 is a schematic diagram of an application state of a microsurgery auxiliary device provided by one embodiment of the present invention in a dental clinic; FIG. 6*a* and FIG. 6*b* are principle schematic diagrams of optical paths of a microsurgery auxiliary device provided by one embodiment of the present invention with dual illumination optical paths; FIG. 7 is a principle schematic diagrams of optical paths of a microsurgery auxiliary device provided by one embodiment of the present invention when a projection lens group and a zoom lens group are linked; FIG. 8 is a schematic diagram of the viewing angle and the distance of a naked eye 3D display of a microsurgery auxiliary device provided by one embodiment of the present invention; FIGS. 9*a*-9*c* are schematic structural diagrams of a microsurgery auxiliary device provided by one embodiment of the present invention when a naked eye 3D display is mounted on a support; FIG. 10*a* and FIG. 10*b* are mounting schematic diagrams of a microsurgery auxiliary device provided by one embodiment of the present invention when a naked eye 3D display is mounted outside a support.

EMBODIMENTS

The present application provides a microsurgery auxiliary device, comprising a lens body 1 and a naked eye 3D display 2. The lens body 1 is internally provided with an imaging unit 10. The imaging unit 10 comprises a large objective lens group 11, a zoom lens group 12, a first tube objective lens 13, and a photosensitive element 14. The large objective lens group 11, the zoom lens group 12, the first tube objective lens 13, and the photosensitive element 14 are sequentially located in the same observation optical path 15, as shown in FIG. 1 or FIG. 2*a* and FIG. 2*b*.

The large objective lens group 11 comprises at least one positive lens group 111 and at least one negative lens group 112. The positive lens group 111 and the negative lens group 112 are arranged in the same optical axis. The distance between the positive lens group 111 and the negative lens group 112 is adjustable, and the adjustment range of the distance between the positive lens group 11 and the negative lens group 112 is not less than 6 mm. The large objective lens with a variable focal length can easily change a focal plane position, i.e., the working distance of operation, to cover a required surgical depth. The implementation is to change the distance between the positive lens group 111 and the negative lens group 112, the adjustment range of the working distance is proportional to the range of the distance between the positive lens group 111 and the negative lens group 112, as shown in FIG. 2*a* and FIG. 2*b*. The positive lens group 111 comprises at least two optical lenses made of different materials. The negative lens group 112 comprises at least two optical lenses made of different materials. The negative lens group 112 is close to an object to be observed, and comprises an outer side surface 1121 and an inner side surface 1122. Both the outer side surface 1121 and the inner side surface 1122 are concave surfaces. An absolute value of radius of curvature of the outer side surface 1121 is smaller than an absolute value of radius of curvature of the inner side surface 1122.

A binocular observation optical path 15 is preferably adopted in the present application. Each observation optical path 15 is internally provided with a zoom lens group 12, a first tube objective lens 13 and a photosensitive element 14. Two observation optical paths 15 share one large objective lens group 11. Two optical paths of zoom lens groups 12 realize observation of different magnifications, and whole and local observation of an affected part can be carried out. The zoom lens group 12 is preferably an afocal Galileo structure, and can be divided into stepped zoom or continuous zoom. When the zoom lens group 12 is of a continuous zoom structure, the zoom lens group 12 comprises at least two groups of second lenses 121. The second lenses 121 can be driven to move along respective optical axis directions. With the combination of the zoom lens group 12 and a large objective lens with a variable focal length, the microsurgery auxiliary device of the present application can conveniently observe tissue structures at different depths with different magnifications.

The microsurgery auxiliary device of the present application further comprises a support 6, the support 6 comprises a base 61, a supporting rod 62 vertically mounted on the base 61, a large cross arm 63 rotatably mounted on the supporting rod 62, a small cross arm 64 rotatably mounted on the large cross arm 63, a balance arm 65 rotatably mounted on the small cross arm 64, and the lens body 1 is mounted on the balance arm 65, as shown in FIG. 4 or FIGS. 9*a*-9*c*.

The naked eye 3D display 2 is connected to the photosensitive element 14. The size of the naked eye 3D display 2 is between 12-16 inches. As shown in FIG. 8, the viewing distance between the naked eye 3D display and an observer 5 is 400-1200 mm. The viewing angle range of the naked eye 3D display is not less than 120 degrees, and preferably, the viewing angle is not less than 90 degrees. The naked eye 3D display can be fixed with different fixing modes according to different field conditions and using habits, and the fixing structure is simple and reliable. For example, the naked eye 3D display may be mounted on the upper surface of the large cross arm 63 and located above the supporting rod 62, as shown in FIG. 9*a*, or may be hung from the lower surface of the large cross arm 63, as shown in FIG. 9*c*, or may be directly mounted on the supporting rod 62, as shown in FIG. 9*b*. The naked eye 3D display, whether mounted on the large cross arm 63 or the supporting rod 62, may be rotatably mounted, fixedly mounted, or detachably or movably mounted. Meanwhile, the naked eye 3D display 2 may not be mounted on the support 6 of the auxiliary device, and may be placed on the ground through the base body 21 and the connecting rod 22, as shown in FIG. 10*a*, or hung on a roof, as shown in FIG. 10*b*. The naked eye 3D display 2 is mounted at one end of the connecting rod 22, and the other end of the connecting rod 22 is movably mounted on the base body 21. The connecting rod 22 can be driven to move relative to the base body 21 along the axis thereof or rotate with the axis thereof as a rotating axis, so as to adjust the mounting position of the naked eye 3D display 2. The naked eye 3D display is arranged within a range of 400-1200 mm, which is close to the observation distance of common clinical equipment. When the observer 5 switches an observation line of sight between the display and other equipment, human eyes do not need to repeatedly focus, time and labor are saved, brightness has no loss, and visual fatigue is reduced. Besides, a closer observation distance is in line with a human eye's habit of approaching when distinguishing details. In the present application, a naked eye 3D display serves as the naked eye 3D display 2, so that the observer 5 can directly perform surgical operations by observing the naked eye 3D display, the overall structure of the device is simple, complex data processing of images is not required, and system delay is small. In addition, with the naked eye 3D display, the observer 5 can clearly observe an object to be observed within a certain range of observation angles without adjusting the orientation of the display. Taking dental clinic as an example, a doctor is usually at the six-o'clock position. When it is necessary to examine or operate maxillary molars temporarily, the doctor may move to the nine-o'clock and three-o'clock positions. At this time, normal observation can also be realized without adjusting the orientation angle of the display, as shown in FIG. 5.

In a further embodiment, the microsurgery auxiliary device further comprises an acquisition device, a processing device and a driving device. The acquisition device can be configured to acquire eye position information of the observer 5. The processing device can be configured to control the driving device to act according to acquired eye position information so as to adjust the display angle of the naked eye 3D display 2, such that the naked eye 3D display 2 automatically tracks eyes of the observer 5 and rotates therewith to ensure an optimal observation angle.

The lens body 1 is further internally provided with at least one illumination unit 3. The illumination light of each illumination unit 3 can illuminate an object to be observed through the large objective lens group 11. The direction of the illumination light entering the large objective lens group 11 is parallel to the direction of the optical axis of the large objective lens group 11. The reflection loss thus can be reduced. Symmetrical dual optical paths 35 may be arranged to enhance illumination intensity, the transverse volume of the system is compressed, and lens body balance is facilitated, as shown in FIG. 6*a* and FIG. 6*b*. The illumination unit 3 comprises a light source assembly 31, a condensing lens group 32, a diaphragm 33, and a projection lens group 34, which are sequentially positioned in the same illumination optical path 35. The light source assembly 31 comprises at least one LED light source 311, and at least one of the LED light sources 311 in the light source assembly 31 can be driven to switch to the illumination optical path 35 to illuminate an object to be observed. For example, apart from a white light source, the light source assembly 31 also comprises at least one monochromatic light source (for a fluorescent mode) which can be switched with the white light source to enter the illumination optical path 35. The projection lens group 34 comprises at least one first lens 341 which can be driven to move along the direction of the optical axis.

In a further embodiment, the microsurgery auxiliary device of the present application may also be provided with a transmission device between the projection lens group 34 and the zoom lens group 12 to enable the linkage of the projection lens group 34 and the zoom lens group 12, as shown in FIG. 7. The transmission device is not shown, and the link relation between the projection lens group 34 and the zoom lens group 12 is schematically shown in a broken line. In the case of observation at a low magnification, the diameter of a field of view of object plane imaging is large, and an illumination optical spot needs to cover the entire object plane field of view at this time. However, when switching to a high magnification, the diameter of the field of view of the object plane is rapidly reduced, and the projection lens group 34 of the illumination optical path 35 is correspondingly adjusted at this time, so that the illumination optical spot can also be reduced accordingly, thereby reducing possible optical damage risks to tissues outside the field of view. At the same time, it is also conducive to improving the illumination inside the field of view and compensating for the reduction of subjective brightness of human eyes during high magnification observation.

In a further embodiment, when necessary, the microsurgery auxiliary device of the present application may also be provided with an observation unit 4 on the lens body 1 to realize conventional visual observation, as shown in FIG. 4. As shown in FIG. 3, the observation unit 4 comprises an eyepiece 41, a turning lens group 42 (or a prism group), and a second tube objective lens 43. The imaging unit 1 further comprises a spectroscope group 16. In the same observation optical path 15, light sequentially passes through the large objective lens group 11 and the zoom lens group 12 to reach the spectroscope group 16. The spectroscope group 16 splits the light into two parts, one part sequentially passes through the first tube objective lens 13 to reach the photosensitive element 14, and the other part sequentially passes through the second tube objective lens 43, the turning lens group 42 and the eyepiece 41. In this way, when in use, the observer 5 can not only observe an object to be observed through the naked eye 3D display 2, but also observe the object to be observed in a conventional visual observation mode, which greatly enhances the operability and adaptability of the microsurgery auxiliary device.

As used herein, the terms "comprise," "include" or any other variations thereof, are intended to cover a non-exclusive inclusion in addition to those elements listed and may also include other elements not expressly listed.

As used herein, positional words such as front, back, upper and lower are defined by positions of parts in drawings and between the parts, which are only for clarity and convenience of expressing the technical solution. It is to be understood that use of such positional words should not limit the protection scope claimed in the present invention.

The embodiments and features in the embodiments described above herein can be combined without conflict.

The above are only preferred embodiments of the present invention, and are not intended to limit the present invention. Any modifications, equivalent substitutions, improvements, and the like within the spirit and the principle of the present invention should be included in the protection scope of the present invention.

What is claimed is:

1. A microsurgery auxiliary device, comprising a lens body and a naked eye 3D display, wherein the lens body is internally provided with an imaging unit, the imaging unit comprises a large objective lens group, a zoom lens group, a first tube objective lens and a photosensitive element, the large objective lens group, the zoom lens group, the first tube objective lens and the photosensitive element are sequentially positioned in the same observation optical path, the large objective lens group comprises at least one positive lens group and at least one negative lens group, the positive lens group and the negative lens group are arranged in the same optical axis, a distance between the positive lens group and the negative lens group is adjustable, the naked eye 3D display is directly connected to the photosensitive element, enabling low system delay between the naked eye 3D display and the photosensitive element and without complex data processing on image captured by the photosensitive element, wherein the microsurgery auxiliary device further comprises an acquisition device, a processing device and a driving device, the acquisition device is to acquire position information of human eyes of an observer, and the processing device is to control the driving device to rotate with the eyes of the observer to ensure that a viewing angle of the observer is in a range of not less than 120 degrees with respect to the naked eye 3D display while a distance between the naked eye 3D display and the observer is in a range of 400-1200 mm.

2. The microsurgery auxiliary device according to claim 1, wherein the positive lens group comprises at least two optical lenses made of different materials, the negative lens group comprises at least two optical lenses made of different materials, the negative lens group is close to an object to be observed, and comprises an outer side surface and an inner side surface, both the outer side surface and the inner side surface are concave surfaces, and an absolute value of radius of curvature of the outer side surface is smaller than an absolute value of radius of curvature of the inner side surface.

3. The microsurgery auxiliary device according to claim 1, wherein the adjustment range of the distance between the positive lens group and the negative lens group is not less than 6 mm.

4. The microsurgery auxiliary device according to claim 1, wherein the lens body is also internally provided with at least one illumination unit, the illumination light of each illumination unit can illuminate an object to be observed through the large objective lens group, and the direction of illumination light entering the large objective lens group is parallel to the direction of an optical axis of the large objective lens group; the illumination unit comprises a light source assembly, a condensing lens group, a diaphragm and a projection lens group which are sequentially positioned in the same illumination optical path; and the light source assembly comprises at least one LED light source, and at least one LED light source in the light source assembly can be driven to be switched to the illumination optical path to illuminate an object to be observed.

5. The microsurgery auxiliary device according to claim 4, wherein the projection lens group comprises at least one first lens, and the first lens can be driven to move along the optical axis direction thereof; and the zoom lens group is of a continuous zoom structure, and comprises at least two groups of second lenses, and the second lenses can be driven to move along respective optical axis directions.

6. The microsurgery auxiliary device according to claim 5, further comprising a transmission device, wherein the projection lens group and the zoom lens group are linked through the transmission device.

7. The microsurgery auxiliary device according to claim 1, wherein the microsurgery auxiliary device has a binocular observation optical path, wherein the microsurgery auxiliary device further comprises an observation unit, the observation unit comprises an eyepiece, a turning lens group and a second tube objective lens, the imaging unit further comprise a beam splitter group, in the same observation optical path, light sequentially passes through the large objective lens group and the zoom lens group to reach the beam splitter group, the beam splitter group splits the light into two parts, one part sequentially passes through the first tube objective lens to reach the photosensitive element, and the other part sequentially passes through the second tube objective lens, the turning lens group and the eyepiece.

8. The microsurgery auxiliary device according to claim 7, further comprising a support, wherein the support comprises a base, a supporting rod vertically mounted on the base, a large cross arm rotatably mounted on the supporting rod, a small cross arm rotatably mounted on the large cross arm, and a balance arm rotatably mounted on the small cross arm, and the lens body and the observation unit are mounted on the balance arm; the naked eye 3D display is mounted on the large cross arm or the supporting rod; or the microsurgery auxiliary device further comprises a base body and a connecting rod mounted on the base body; and the naked eye 3D display is mounted at one end of the connecting rod, and can be placed on the ground or hung on a roof through the base body and the connecting rod.

9. The microsurgery auxiliary device according to claim 8, wherein the other end of the connecting rod is movably mounted on the base body, the connecting rod can be driven to move along the axial direction thereof and/or the connecting rod can be driven to rotate by taking the axis thereof as a rotating shaft.

10. The microsurgery auxiliary device according to claim 1, wherein the size of the naked eye 3D display is between 12-16 inches; and the processing device can be configured to control the driving device to act according to the acquired position information of the human eyes so as to adjust a display angle of the naked eye 3D display.

* * * * *